United States Patent [19]

Hashimoto et al.

[11] Patent Number: 5,298,038
[45] Date of Patent: Mar. 29, 1994

[54] GUERBET BRANCHED ALKOXYLATED AMINE DETERGENT ADDITIVES

[75] Inventors: Jiro Hashimoto; Shogo Nomoto, both of Wakayama, Japan

[73] Assignee: Kao Corporation, Tokyo, Japan

[21] Appl. No.: 764,955

[22] Filed: Sep. 25, 1991

Related U.S. Application Data

[63] Continuation of Ser. No. 383,044, Jul. 21, 1989, abandoned.

[30] Foreign Application Priority Data

Aug. 5, 1988 [JP] Japan .................. 63-195799
Mar. 3, 1989 [JP] Japan .................... 1-51222

[51] Int. Cl.$^5$ ............................................. C10L 1/22
[52] U.S. Cl. ......................................... 44/433; 44/399;
44/416; 44/418; 44/419; 44/422; 44/423; 44/434
[58] Field of Search ............... 44/399, 416, 418, 419, 44/422, 423, 433, 434

[56] References Cited

U.S. PATENT DOCUMENTS

| | | | |
|---|---|---|---|
| 2,443,796 | 6/1948 | Martin et al. | |
| 2,854,324 | 9/1958 | Shen et al. | 44/399 |
| 2,996,365 | 8/1961 | De Groote et al. | 44/399 |
| 3,063,819 | 11/1960 | Watt et al. | 44/399 |
| 3,117,931 | 1/1964 | Westlund et al. | |
| 3,437,466 | 4/1969 | Betty et al. | |
| 3,542,678 | 11/1970 | Bork | 44/399 |
| 3,787,354 | 1/1974 | Cyba | |
| 3,920,729 | 11/1975 | Sagawa et al. | 44/399 |
| 3,980,450 | 9/1976 | Battersby et al. | 44/433 |
| 3,982,909 | 9/1976 | Hollyday, Jr. | 44/399 |
| 4,204,481 | 5/1980 | Malec | 44/66 |
| 4,273,721 | 6/1981 | Nersesian | 260/404 |
| 4,477,261 | 10/1984 | Sung | 44/419 |
| 4,613,343 | 9/1986 | Horodysky et al. | 44/419 |
| 4,622,047 | 11/1986 | Bernasconi et al. | 44/71 |
| 4,639,256 | 1/1987 | Axelrod et al. | 44/399 |
| 5,089,029 | 2/1992 | Hashimoto et al. | 44/433 |
| 5,094,667 | 3/1992 | Schilowitz et al. | 44/434 |

FOREIGN PATENT DOCUMENTS

| | | |
|---|---|---|
| 0100665 | 2/1984 | European Pat. Off. |
| 0189042 | 7/1986 | European Pat. Off. |
| 0193065 | 9/1986 | European Pat. Off. |
| 0237356 | 9/1987 | European Pat. Off. |
| 2407258 | 5/1979 | France ................. 44/418 |
| 85-02173 | 5/1985 | PCT Int'l Appl. |
| 1153024 | 5/1969 | United Kingdom. |
| 1549123 | 7/1979 | United Kingdom. |

*Primary Examiner*—Jerry D. Johnson
*Attorney, Agent, or Firm*—Birch, Stewart, Kolasch & Birch

[57] ABSTRACT

An additive for fuel oil comprises a compound comprising (a) an alkyl group having 9 to 37 carbon atoms and containing a branched alkyl having 3 to 18 carbon atoms and (b) an amine group having at least one polyoxyalkylene having 2 to 4 carbon atoms or an aminoxide having at least one polyoxyalkylene having 2 to 4 carbon atoms. This additive is effective for cleaning the injection nozzle of coking.

4 Claims, No Drawings

GUERBET BRANCHED ALKOXYLATED AMINE DETERGENT ADDITIVES

This application is a continuation of application Ser. No. 07/383,044 filed on Jul. 21, 1980, now abandoned.

BACKGROUND OF THE INVENTION

1. Field of the Invention

The invention relates to an additive for fuel and a fuel composition comprising said additive. Fuel includes gasoline, light oil which is useful for a Diesel engine and, heavy oil which is used for an internal combustion engine. The invention provides an improvement in view of cleaning the fuel system and the combustion chamber of an internal combustion engine.

2. Statement of prior arts

It is known that when the fuel system and deposits in the combustion chamber of an internal combustion engine an engine will not perform well and the exhaust gas emitting therefrom, will contain undesirable matters.

Fuel cleaning agents, and in particular, gasoline cleaning agents are added to gasoline for the purpose of removing deposits from the gasoline air intake system, such as the carburetor and intake valves, and preventing the accumulation of deposits, as well as cleaning the inside of the combustion chambers. Deposits that have formed on the intake valves and intake ports cause a decrease in engine horsepower, a worsening of performance and an increase in the amount of exhaust gas. In recent years, the performance capabilities of engines are continuously increasing and as a result, they have become more sensitive to these types of deposits. Further, deposits that accumulate in the injection nozzles of fuel injection engines that have become quite popular in recent years are a particular problem. In other words, since the fuel flowpath in such injection nozzles is quite narrow, if deposits should happen to form on the inside of these flowpaths, the injection pattern of the fuel becomes distorted, causing the appearance of serious detrimental effects such as defective startability, poor operating performance and decreased engine horsepower. In addition, this also brings about other negative effects including poor fuel consumption and increased amounts of exhaust gas.

Various types of fuel additives have been proposed in order to solve these types of problems. As an example, ether amine has been disclosed in the specifications of U.S. Pat. No. 3,849,083 and Patent Journal Patent Disclosure No. SHO 57-24398. Although this ether amine is used as a cleaning agent for the carburetor, its cleaning action on parts of the intake system, other than the carburetor, are small.

Stains, in particular coking, in an injection nozzle of a Diesel engine, also have an influence on performance. Coking makes exhausted gas black, increases the amount of sulfates coming from the sulfur in the fuel and increases the amount of hydrocarbon matters caused by partial combustion of the fuel and the lubricant. In this way, particulates are increased. The Japanese patent publication A 62-68891 discloses the use of an oxyalkylene compound of an alkylamine to solve that problem. In the reference, it is not seen that cleaning in the injection nozzle can be achieved. Further U.S. Pat. Nos. 3,478,096 and 3,637,358 disclose the use of an alkylether amine which is effective in stabilizing the fuel, but does not work for cleaning of the injection nozzle.

SUMMARY OF THE INVENTION

The invention provides an additive for fuel and fuel composition comprising said additive and an improvement in view of cleaning the fuel system and the combustion chamber of an internal combustion engine.

The invention provides an additive for fuel oil comprising a compound comprising (a) an alkyl group having 9 to 37 carbon atoms and containing a branched alkyl having 3 to 18 carbon atoms and (b) an amine group having at least one polyoxyalkylene having 2 to 4 carbon atoms or an amineoxide having at least one polyoxyalkylene having 2 to 4 carbon atoms. The additive is effective for cleaning the injection nozzle of coking.

The additive of the invention may be defined by the formula (7), (8) or (9):

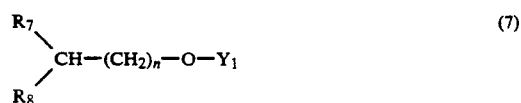

(7)

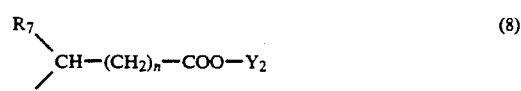

(8)

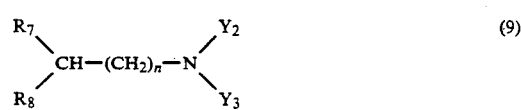

(9)

in which R7 and R8 are each a hydrocarbon group having 3 to 18 carbon atoms, provided that the sum total of the carbon number in R7 and R8 ranges from 8 to 36, n is zero or an integer of 1 to 4, Y1 is an amine group having the formula (10) or an amineoxide group having the formula (11), Y2 is hydrogen or has the formula (12) or (13), with the proviso that Y2 cannot be hydrogen in forming (8), and Y3 has the formula (12) or (13):

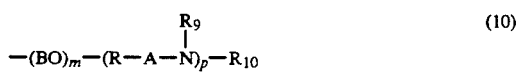

(10)

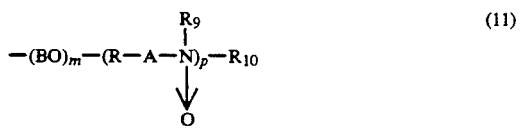

(11)

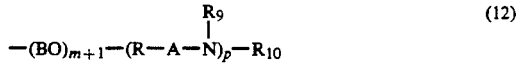

(12)

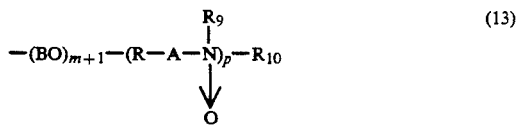

(13)

in which B is an alkylene having 2 to 4 carbon atoms, m is zero or an integer of 1 to 3, R does not exist or is —CH2CONH—, —CH2CH(OH)— or —CH2CO—, A does not exist or is an alkylene having 1 to 4 carbon atoms, R9 and R10 are each hydrogen, an alkyl having 1 to 4 carbon atoms or a hydroxyalkyl having 1 to 4 carbon atoms and p is 1 or 2.

The additive of the invention includes two embodiments having the formula (1) or (2), respectively.

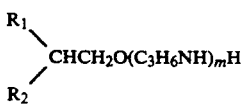  (1)

in which R1 and R2 are each a hydrocarbon group having 3 to 16 carbon atoms, provided that the sum total of the carbon number in R1 and R2 ranges from 10 to 32, and m is 1 or 2,

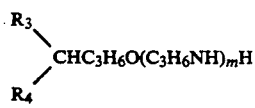  (2)

in which R3 and R4 are each a hydrocarbon group having 3 to 15 carbon atoms, provided that the sum total of the carbon number in R3 and R4 ranges from 8 to 30, and m is 1 or 2.

It is preferable that a mixture of the compound in which R7 and R8 are straight chain and the other compound in which R7 and R8 contains a branched methyl.

The invention provides a fuel composition which comprises fuel and the additive as defined above. The fuel may be a mineral oil or a synthesized oil.

In the additive compound of the invention preferably having the formula (7), (8) or (9), R7 and R8 may be a straight chain hydrocarbon group or a branched chain hydrocarbon group. The straight hydrocarbon group includes n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl and n-hexadecyl. The branched chain hydrocarbon group includes iso-propyl, iso-butyl, iso-penatyl, 1-methylbutyl, 2-methylbutyl, 3-methylbutyl, 4-methylpentyl, 5-methylhexyl, 1,1,3-trimethylbutyl, 1,3,3-trimethylbutyl, 3-methylhexyl, 1,2,4-trimethylpentyl, 1,3-dimethylhexyl, 3,3,5-trimethylhexyl, 3,5,5-trimethylhexyl, 3,4,6-trimethylheptyl, 3,5,6-trimethylheptyl, 3,5-dimethyloctyl, 1,3,4,6-tetramethylheptyl, 1,1,3,5,5-pentamethylhexyl, 1,4,7-trimethyloctyl, 1,3,3,6-tetramethylheptyl, 3,5,6,8-tetramethylnonyl, 3,3,5,7-pentamethyloctyl, 3,6,9-trimethyldecyl, 1,2,4,6,8-pentamethylnonyl and 4,5,7,9,11-pentamethylundecyl.

It is essential in the invention that the sum total of the number of carbons contained in the alkyl group, preferably defined by —CHR7R8, ranges from 9 to 37. When it is less than 9, the cleaning effect is not attained. When it is more than 37, the solubility of the additive compound in fuel decreases and then thermal residues can be formed. A greater improvement of the invention can be obtained when it especially ranges from 10 to 32.

In the formulae (7) to (13), BO shows an oxyalkylene or an oxyalkylene ether. It is preferable that the alkylene for B has 2 to 4 carbon atoms and includes ethylene, propylene, 1,2-butylene, 2,3-butylene, 1,3-butylene and 1,4-butylene. A mixture of two or more kinds types of alkylene may be used here. When m is more than 3, the additive cannot prevent the resulting fuel composition from emulsion by water involved. The additive compound of the invention prevents fuel from emulsifying when the fuel contains water.

The additive compound in which R does not exist and A is an alkylene having 3 carbon atoms can be produced, for example, by cyanoethylating a branched alcohol such as shown by the formula (7), (8) or (9) in which Y1 is —(BO)m—H, Y2 and Y3 are —(BO)m+1—H, with acrylonitrile and then hydrogenating the product. Further cyanoethylation and hydrogenation may be repeated with the product. Cyanoethylation is conducted, while heating and agitating, with a catalyst of a strong alkali such caustic soda. Hydrogenation is carried out with a hydrogenation catalyst such as Raney nickel.

In another preparation method, a halogenated compound such as R7R8CH—(CH2)n-X, in which X is a halogen, and a compound of HOY1, H—COO—Y2 or HNY2Y3 are reacted with each other, in the presence of an alkali metal or an alkoxide with an alkaline earth metal, an oxide thereof or a hydroxide thereof.

When R in Y1, Y2 and Y3 is —CH2CONH—, ≧CH2CH(OH)— or —CH2CO— in the formula (7), (8) or (9), the additive can be produced by reacting a branched alcohol having the below shown formula (14), (15) or (16), respectively, with chloroacetic acid or epichlorohydrin and then reacting the resulting product with a corresponding amine compound and/or adding an alkylene(C2 to C4) oxide thereto.

When R does not exist in the formulae (7) to (9), the additive (7) to (9) can be produced by halogenating a branched alcohol shown below at its terminal hydroxyl group with a halogen compound such as phosphorus tribromide and then reacting the resulting product with a corresponding amine compound and/or adding an alkylene oxide thereto.

When Y1 is —(BO)m—RA—N(—O)R9R10 and Y2 and Y3 are each —(BO)m+1RA—N(—O)R9R10, the compound (7) to (9) can be produced by reacting a compound in which Y1 is —(BO)m—RANR9R10 or Y2 and Y3 are each —(BO)m+1-RANR9R10 with an organic peroxide.

Another method for synthesizing the compound can be adopted here.

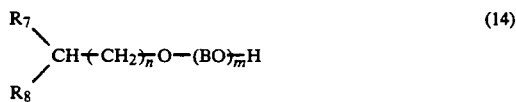  (14)

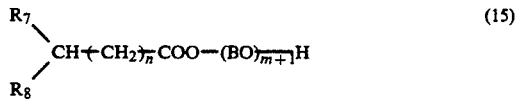  (15)

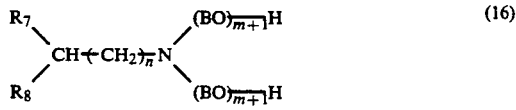  (16)

Here, it is necessary that the branched alcohol which serves as a raw material of this invention be a compound like that indicated in general formula (5) and general formula (6) indicated below.

  (5)

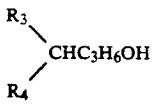 (6)

($R_1$ and $R_2$ are hydrocarbon residues having 3-16 carbon atoms where the sum of the carbon atoms of $R_1$ and $R_2$ is from 10 to 32, and $R_3$ and $R_4$ are hydrocarbon residues having 3 to 15 carbon atoms where the sum of the carbon atoms of $R_3$ and $R_4$ is from 8 to 30.)

These types of alcohols are referred to as large branched alcohols, and as an example, can be directly obtained using the Gerbe reaction by condensing two molecules of a natural or synthetic aliphatic alcohols. These can also be obtained by reduction of a branched fatty acid obtained in a reaction between acetic anhydride and an α-alcohol.

Specific examples of alcohols that can be used as raw materials of this invention include 2-methyldodecyl alcohol, 2-butylhexadecyl alcohol, 2-hexyloctyl alcohol, 2-hexyldecyl alcohol, 2-hexyltetradecyl alcohol, 2-hexyloctadecyl alcohol, 2-heptylnonyl alcohol, 2-heptylundecyl alcohol, 2-octyldodecyl alcohol, 2-nonylundecyl alcohol, 2-nonyltridecyl alcohol, 2-decyldodecyl alcohol, 2-decyltetradecyl alcohol, 2-decyloctadecyl alcohol, 2-undecylpentadecyl alcohol, 2-dodecyltetradecyl alcohol, 2-dodecylhexadecyl alcohol, 2-tridecylheptadecyl alcohol, 2-tetradecylhexadecyl alcohol, 2-tetradecyloctadecyl alcohol, 2-hexadecyloctadecyl alcohol, 4-hexyldodecyl alcohol, 4-octyltetradecyl alcohol, 4-nonylpentadecyl alcohol, 4-decylhexadecyl alcohol, 4-dodecyloctadecyl alcohol,

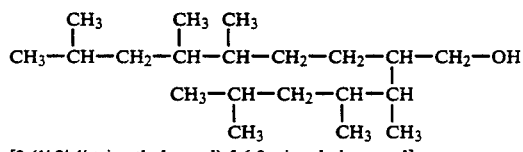

[2-(1',2',4'-trimethylpentyl)-5,6,8-trimethylnonanol],

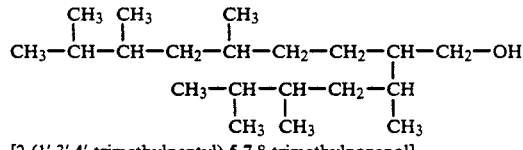

[2-(1',3',4'-trimethylpentyl)-5,7,8-trimethylnonanol],

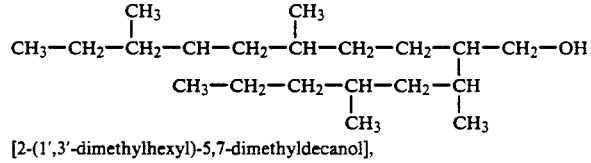

[2-(1',3'-dimethylhexyl)-5,7-dimethyldecanol],

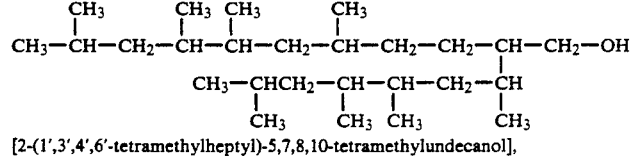

[2-(1',3',4',6'-tetramethylheptyl)-5,7,8,10-tetramethylundecanol],

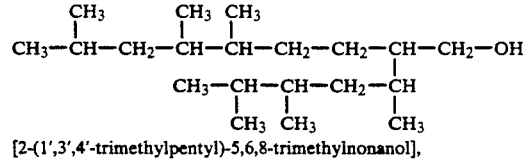

[2-(1',3',4'-trimethylpentyl)-5,6,8-trimethylnonanol],

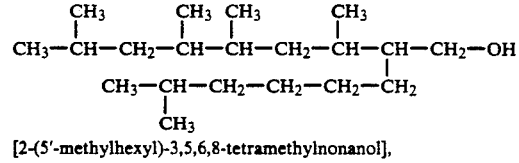

[2-(5'-methylhexyl)-3,5,6,8-tetramethylnonanol],

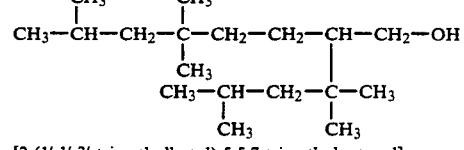

[2-(1',1',3'-trimethylbutyl)-5,5,7-trimethyloctanol],

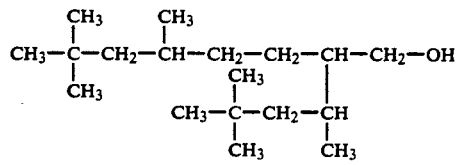
[2-(1',3',3'-trimethylbutyl)-5,7,7-trimethyloctanol],

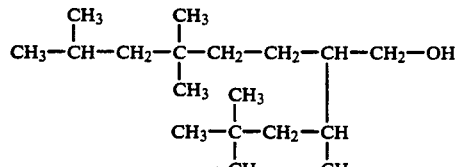
[2-(1',3',3'-trimethylbutyl)-5,5,7-trimethyloctanol],

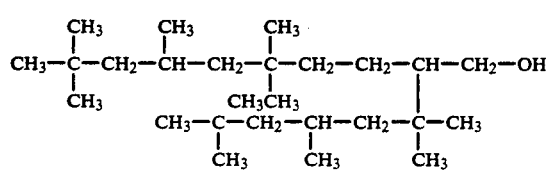
[2-(1',1',3',5',5'-pentamethylhexyl)-5,5,7,9,9-pentamethyldecanol],

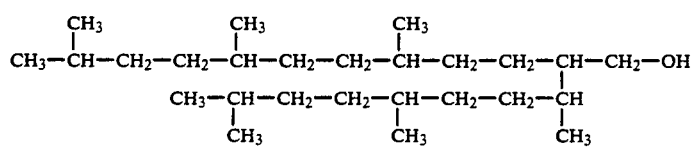
[2-(1',4',7'-trimethyloctyl)-5,8,11-trimethyldodecanol],

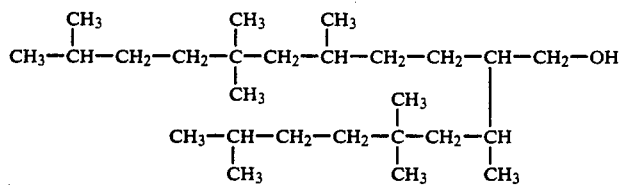
[2-(1',3',3',6'-tetramethylheptyl)-5,7,7,10-tetramethylundecanol],

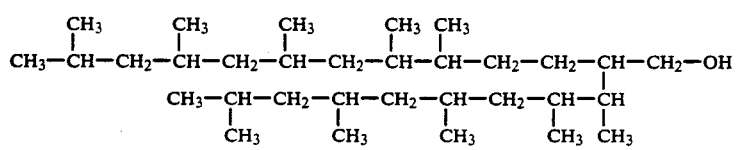
[2-(1',2',4',6',8'-heptamethylnonyl)-5,6,8,10,12-heptamethyltridecanol],

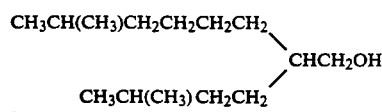
[2-(3'-methylbutyl)-7-methyloctanol], and

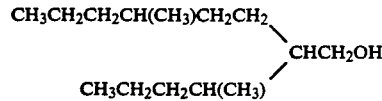
[2-(1'-methylbutyl)-5-methyloctanol].

In regard to the chain length of these large branched alcohols, the sum of the carbon atoms of $R_1$ and $R_2$ is from 10 to 32 and more preferably, from 12 to 30. If the sum of the number of carbon atoms is less than 10, the dispersion force of the alkylether amine that is obtained with respect to sludge is eliminated which is not preferable. The sum of the number of carbons of $R_3$ and $R_4$ is from 8 to 30 and more preferably, from 10 to 28. Here also, if the sum of the number of carbon atoms is less than 8, the sludge dispersion properties become poor. In addition, in the case the sum of the number of carbons described above is too large, the solubility of the alkylether amine that is obtained in gasoline is reduced which prevents it from being used.

In the case of alkylether amines which have for example as their raw material alcohol, non-branched, straight-chain alcohols or oxoalcohols, etc. which contain small branched alcohols made up of methyl groups, etc., not only do such alkylether amines have poor solubility in fuel, they also have markedly inferior effects with respect to the properties which are the objective of this invention, such as cleaning properties and thermal decomposition properties.

In consideration of such properties, it is necessary that the carbon chain length of the $R_1$ and $R_2$ portions be from 3 to 16, and that of the $R_3$ and $R_4$ portions be from 3 to 15. In particular, in the case the number of carbons of $R_1$ and $R_2$ is from 6 to 12 and the sum of the number of carbons of $R_1$ and $R_2$ is from 12 to 22, or in the case the number of carbons of $R_3$ and $R_4$ is from 5 to 11 and the sum of the number of carbons of $R_3$ and $R_4$ is from 11 to 21, more preferable effects can be obtained. If the chain length becomes too large, its the solubility in gasoline undesirably decreases as indicated above.

For a starting material which satisfies the criteria indicated above, a large branched alcohol which is obtained by reacting alcohols of homogeneous or heterogeneous composition in a Gerbe reaction is most desired.

The compound having the formula (2) can be obtained by cyanoethylation and hydrogenation, optionally including further cyanoethylation and reduction, of a starting material of one or more alcohols having a large group of a branched alkyl, as shown above, or an alkyleneoxide adduct of the alcohol.

The additive compound having the formula (2) provides an improvement in the cleaning effect. In particular, the additive compound having a branched hydrocarbon group of R1 to R4 is more effective for this purpose. A mixture of a compound in which R1 to R4 are each a straight chain hydrocarbon group and another compound in which R1 to R4 are each a branched chain hydrocarbon group provides a more improved effect in view of the cleaning. The mixture is preferred to have a weight ratio of the former to the latter in the range between 0.02 and 50, more preferably between 0.1 and 10.

Although raw material alcohols having small branched chain portions in addition to large branched chain portions $R_1$ -$R_4$ are as indicated above, those alcohols that in particular have methyl branched chains for the small branched chain portions are preferable. These types of large branched chain alcohols can be easily obtained by synthesis from oxoalcohols of dimers, trimers, tetramers or pentamers of propylene, oxoalcohols of dimers or trimers of butylene, isobutylene, etc., or a mixture of these using a Gerbe reaction.

It is preferable to use the additive of the invention together with a carrier oil such as mineral oil and a synthesized oil to therefore improve the removal of deposits and retain the cleaning effect. The synthesized oil is more preferable and includes an olefin polymer such as poly-alpha-olefin and polybutene, an alkyleneoxide adduct of an alcohol or an alkylphenol and a polymer of an alkyleneoxide. An adduct of an alkyleneoxide such as propyleneoxide and butyleneoxide, an ester thereof and an etherized product thereof are more preferred. The carrier oil is preferred to be used in an amount of 0.05 to 20 parts by weight per 1 part by weight of the additive compound. Examples of the synthesized oil are illustrated below. These are preferably used in an amount of 0.1 to 10 parts by weight per 1 part by weight of the additive. In the formulae, R5 and R6 each are an alkyl having 1 to 30 carbon atoms, R' is hydrogen or an alkyl having 1 to 20 carbon atoms, A is an alkylene having 3 or 4 carbon atoms and d is an integer of 1 to 50.

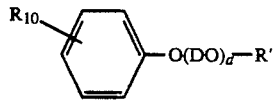

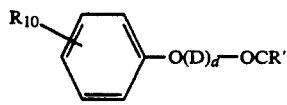

In the invention, an unexpected improvement in the dispersion of sludges, removal of deposits and decrease of thermal residues and solubility in fuel is obtained because the additive compound has a large branched chain, an ether group and an amino group or a derivative thereof in its chemical structure.

The additive compound is preferably used in an amount of 0.1 to 50,000 ppm in this fuel. In the range, in the greater than amount the additive used, the greater the cleaning effect is. From a practical point of view, the range of 1 to 20,000 ppm is useful.

The additive of the invention may be used with another additive for fuel such as anti-corrosive, an anti-emulsifying agent and a metal-inactivating agent.

EMBODIMENTS

The following provides a more detailed description of examples of synthesis and embodiments of this invention. However, this invention is not limited to these syntheses and embodiments.

SYNTHESIS 1

400 g of 2-octyldodecyl alcohol was placed in a 1 liter, 4-necked flask. 83.85 g of acrylonitrile was dropped in over the course of 3 hours while heating and stirring at a temperature of 76°–80° C. in a nitrogen atmosphere with 0.222 g of potassium hydroxide as the catalyst. Following dropping in of the acrylonitrile, the mixture was allowed to react for 2 hours at 76°–80° C. Next, the potassium hydroxide was neutralized with acetic acid and the excess acrylonitrile was removed by distillation under a reduced pressure to obtain the azoethylate.

300 g of this azoethylate was placed in a 1 liter autoclave after which hydrogenation was performed applying a hydrogen pressure of 20 kg/cm² using Raney nickel as the catalyst to obtain 2-octyldodecyloxypropylamine represented with the formula $C_{10}H_{17}CH(C_5H_{17})CH_2OC_3H_6NH_2$.

SYNTHESIS 2

Synthesis was performed in the same manner as Synthesis 1 using 2-tetradecyloctadecyl alcohol as the raw material alcohol to obtain 2-tetradecyloctadecyloxypropylamine represented with the formula $C_{16}H_{33}CH(C_{14}H_{27})CH_2C_3H_6NH_2$.

SYNTHESIS 3

Following azoethylation of the 2-tetradecyloctadecyloxypropylamine obtained in Synthesis 2 using the same method as that of Synthesis 1, hydrogenation was performed to obtain 2-tetradecyloctadecyloxypropylpropylenediamine represented with the formula $C_{16}H_{33}CH(C_{14}H_{27})CH_2O(C_3H_6NH_2)_2H$.

SYNTHESIS 4

Synthesis was performed in the same manner as that of Synthesis 1 using 2-decyltetradecyl alcohol as the raw material alcohol to obtain 2-decyltetradecyloxypropylamine represented with the formula $C_{12}H_{25}CH(C_{10}H_{21})CH_2OC_3H_6NH_2$.

SYNTHESIS 5 n-octyl alcohol and n-decyl alcohol were allowed to react in a Gerbe reaction at a mole ratio of 1:1. A large branched alkoxypropylamine was obtained using the method of synthesis the same as that of Synthesis 1 from the mixed large branched alcohol that was obtained from the above reaction.

SYNTHESIS 6

The large branched alkoxypropylamine represented with the formula indicated below having the typical structure of:

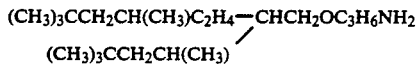

was obtained using the method of synthesis the same as that of Synthesis 1 from Fineoxycol 180 manufactured by Nissan Chemical Industries, Ltd.

SYNTHESIS 7

The large branched alkoxypropylamine represented with the formula:

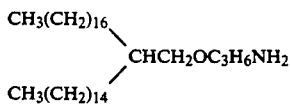

was obtained using the same synthesis method as that of Synthesis 1 using 2-pentadecanylnonadecanol as the raw material alcohol.

SYNTHESIS 8

The large branched alkoxypropylamine represented with the formula:

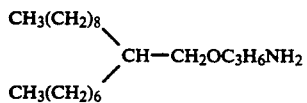

was obtained using the same synthesis method as that of Synthesis 1 using 2-peptylundecanol as the raw material alcohol.

SYNTHESIS 9

The large branched alkoxypropylamine represented with the formula:

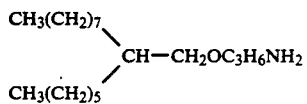

was obtained using the same synthesis method as that of Synthesis 1 using 2-hexyldecanol as the raw material alcohol.

SYNTHESIS 10

The large branched alkoxypropylamine represented with either of the formulae below having the typical structure

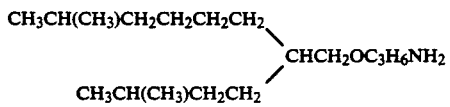

or:

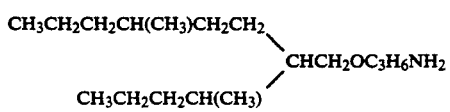

was obtained using the synthesis method the same as that of Synthesis 1 using Nissan Fineoxycol 140 having the typical structure of:

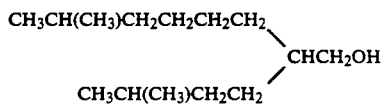

or:

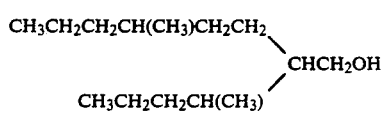

as the raw material alcohol.

SYNTHESIS 11

2-methylnonadecyloxypropylamine represented with the formula $C_{17}H_{35}CH(CH_3)CH_2OC_3H_6NH_2$ was obtained using the same synthesis methods as that of Synthesis 1 using 2-methylnonadecyl alcohol as the raw material alcohol.

SYNTHESIS 12 n-dococyloxypropylamine represented with the formula $n\text{-}C_{22}H_{45}OC_3H_6NH_2$ was obtained using the same synthesis method as that of Synthesis 1 using n-dococyl alcohol as the raw material alcohol.

SYNTHESIS 13

62.5g of (2-aminoethyl) ethanolamine, 8g of magnesium powder and 500ml of xylene were placed in a 1 liter three-necked flask and refluxed for 2 hours. 132g of chlorinated polybutene (MW950) dissolved in 100ml of xylene were then gradually added to the above and refluxed for 6 hours. After cooling, filtering and washing the precipitate that was produced, the precipitate was dried under a reduced pressure to obtain polyisobutenyloxyethylethyleneamine represented with the formula poly-iBu-$OC_2H_4NHC_2H_4NH_2$ (poly iBu: polyisobutynyl group, MW950).

TABLE 1

| # | Structure |
|---|---|
| 14 | CH₃(CH₂)₈\\_CHCH₂O(CH₂CH₂O)₂CH₂CH₂CH₂NH₂ / CH₃(CH₂)₆/ |
| 15 | (CH₃)₃CCH₂CH(CH₃)CH₂CH₂\\_CHCOOCH₂CH₂OCH₂CH₂CH₂NH₂ / (CH₃)₃CCH₂CH(CH₃)/ |
| 16 | CH₃(CH₂)₉\\_CHCH₂CH₂O(CH₂CH₂O)₃CH₂CONHCH₂CH₂N(CH₃)₂ / CH₃(CH₂)₇/ |
| 17 | CH₃(CH₂)₉\\_CHCH₂O(CH₂CH₂O)₂CH₂CH(OH)CH₂N(CH₃)₂ / CH₃(CH₂)₇/ |
| 18 | CH₃(CH₂)₈\\_CHCH₂OCH₂CH₂OCH₂CH₂N(CH₃)₂ / CH₃(CH₂)₆/ |
| 19 | CH₃(CH₂)₁₂\\_CHCH₂CH₂O(CH₂CH(CH₃)O)₂CH₂CH(CH₃)N(CH₃)₂→O / CH₃(CH₂)₁₀/ |
| 20 | CH₃(CH₂)₈\\_CHCH₂CH₂OCH₂CON(CH₃)₂ / CH₃(CH₂)₉/ |
| 21 | CH₃CH(CH₃)CH₂CH₂CH₂CH₂\\_CHCOOCH₂CH₂OCH₂CH₂N(CH₃)₂ / CH₃CH(CH₃)CH₂CH₂/ |
| 22 | CH₃(CH₂)₁₀\\_CHCH₂CH₂N[(CH₂CH₂O)₂CH₂CH₂CH₂NH₂]₂ / CH₃(CH₂)₈/ |
| 23 | CH₃(CH₂)₁₆\\_CHO(CH₂CH₂O)₂CH₂CH₂CH₂N(CH₂CH₂OH)₂ / CH₃(CH₂)₆/ |
| 24 | CH₃(CH₂)₈\\_CHCH₂O(CH₂CH(CH₃)O)₂CH₂CONHCH₂CH₂N(CH₃)₂ / CH₃(CH₂)₆/ |
| 25 | (CH₃)₃CCH₂CH(CH₃)C₂H₄\\_CHCH₂N[CH₂CH₂OCH₂CH₂N(CH₃)₂→O]₂ / (CH₃)₃CCH₂CH(CH₃)/ |
| 26 | CH₃(CH₂)₄\\_CHCH₂OCH₂CH₂N[(CH₂CH₂O)₂H]₂ / CH₃(CH₂)₁₄/ |

EMBODIMENT 1

A dispersion test was performed according to the method indicated below in order to evaluate the sludge deposition prevention and removal effects of the additives obtained in Syntheses and the compounds 14 to 21.

The hexane-insoluble, chloroform-soluble components of sludge that was scraped from the crankcases of engines that were run for a high number of miles were added to a typical base gasoline containing the test additives, in the form of a chloroform solution of sludge in an amount of 600 ppm of sludge.

The amount of sludge 30 minutes after addition of the sludge solutions was investigated at additive concentrations of 100 ppm, 200 ppm and 400 ppm.

Results were evaluated in the form of 3 levels, indicating "○" in the case of no deposition of sludge, a "Δ" in the case of slight deposition of sludge, and a "X" in the case of a large amount of deposited sludge. With no additive, the sludge is insoluble in gasoline and precipitates.

Results are shown in Table 2.

It is seen that the data of the invention show an improvement in dispersion of sludge.

TABLE 2

| | additive | | amount (ppm) 100 | 200 | 400 |
|---|---|---|---|---|---|
| the invention | synthesis | 1 | Δ | ○ | ○ |
| | | 2 | Δ | ○ | ○ |
| | | 3 | ○ | ○ | ○ |
| | | 4 | ○ | ○ | ○ |
| | | 5 | Δ | ○ | ○ |
| | | 6 | Δ | ○ | ○ |
| | | 7 | Δ | Δ | ○ |
| | | 8 | ○ | ○ | ○ |
| | | 9 | Δ | ○ | ○ |
| | | 10 | Δ | ○ | ○ |
| | compound | 14 | ○ | ○ | ○ |
| | | 15 | Δ | ○ | ○ |
| | | 16 | Δ | ○ | ○ |
| | | 17 | Δ | ○ | ○ |
| | | 18 | ○ | ○ | ○ |
| the invention | compound | 19 | Δ | Δ | ○ |
| | | 20 | Δ | ○ | ○ |
| | | 21 | Δ | Δ | ○ |
| | | 22 | Δ | ○ | ○ |
| | | 23 | ○ | ○ | ○ |
| | | 24 | Δ | Δ | ○ |
| | | 25 | Δ | Δ | ○ |
| | | 26 | Δ | ○ | ○ |
| control | synthesis | 11 | X | X | Δ |
| | | 12 | X | X | Δ |
| | | 13 | X | Δ | Δ |

EMBODIMENT 2

A thermal decomposition test was performed according to the method indicated below in order to investigate whether or not the additive itself was deposited in the combustion chamber.

Approximately 1 g (50% kerosene solution) of the additive samples were accurately weighed and placed in an aluminum weighing cup. The samples were then heated for 15 hours at a temperature of 200° C. in a constant temperature bath after which the residual amounts of the additives were measured. The decomposition ratio was calculated with the equation below indicating the weight of the additive sample with "$W_i$" and the residual weight of the additive sample with "$W_r$".

Decomposition Ratio
$(\%) = (W_i - W_r - W_i/2)/(W_i/2) \times 100$

In addition, the appearance of the residue was also observed with the naked eye. The results that were obtained are indicated in Table 3.

TABLE 3

| Type of Additive | Decomposition Ratio (%) | Appearance of Residue |
|---|---|---|
| Products of this Invention: | | |
| Synthesis 1 | 84 | Pale lacquer-like |
| Synthesis 2 | 60 | " |
| Synthesis 3 | 60 | " |
| Synthesis 4 | 70 | Lacquer-like |
| Synthesis 5 | 78 | " |
| Synthesis 6 | 75 | " |
| Synthesis 7 | 58 | " |
| Synthesis 8 | 80 | Pale lacquer-like |
| Synthesis 9 | 75 | " |
| Synthesis 10 | 85 | " |
| Comparative Products: | | |
| Synthesis 11 | 50 | Lacquer-like |
| Synthesis 12 | 45 | Tar-like |
| Synthesis 13 | 25 | " |

As is clear from Table 3, the products of this invention demonstrate superior thermal decomposition in comparison to the comparative products.

EMBODIMENT 3

Depending on the specific additive, emulsification may occur when water becomes mixed into the gasoline in the gasoline tank resulting in a potential problem.

Therefore, a moisture separation test was conducted according to the method indicated below in order to confirm the effectiveness of the additives on a water-gasoline system.

80 ml of gasoline having a sample additive concentration of 200 ppm and 20 ml of pure water were placed in a measuring cylinder equipped with a common stopper and then shaken by hand for 1 minute. Readings were then taken of the fuel phase and the interface after 5, 10, 15 and 30 minutes. The reading standards are as indicated below.

Fuel Phase:
1 = Transparent and glossy
2 = Slightly cloudy
3 = Cloudy
4 = Very cloudy
5 = Emulsion Interface:
1 = Colorless and transparent
1B = Less than 50% of the interface is coated with a small amount of small bubbles
2 = Small bubbles or string-like emulsified fragments are present on 50% or more but less than 100% of the interface
3 = Large string-like emulsified fragments are present over the entire interface but are less than 1 ml
4 = Less than 3ml of scum is present
5 = 3 ml or more of scum is present The results of this test are indicated in Table 4.

TABLE 4

| | Moisture Separation | | | | | | | |
|---|---|---|---|---|---|---|---|---|
| Type of Additive | 5 Min. F | I | 10 Min. F | I | 15 Min. F | I | 30 Min. F | I |
| Products of this Invention: | | | | | | | | |

TABLE 4-continued

| Type of Additive | Moisture Separation | | | | | | | |
|---|---|---|---|---|---|---|---|---|
| | 5 Min. | | 10 Min. | | 15 Min. | | 30 Min. | |
| | F | I | F | I | F | I | F | I |
| Synthesis 1 | 1 | 1 | 1 | 1 | 1 | 1 | 1 | 1 |
| Synthesis 2 | 1 | 1 | 1 | 1 | 1 | 1 | 1 | 1 |
| Synthesis 3 | 1 | 1 | 1 | 1 | 1 | 1 | 1 | 1 |
| Synthesis 4 | 1 | 1 | 1 | 1 | 1 | 1 | 1 | 1 |
| Synthesis 5 | 1 | 1 | 1 | 1 | 1 | 1 | 1 | 1 |
| Synthesis 6 | 1 | 1 | 1 | 1 | 1 | 1 | 1 | 1 |
| Synthesis 7 | 1 | 1 | 1 | 1 | 1 | 1 | 1 | 1 |
| Synthesis 8 | 1 | 1 | 1 | 1 | 1 | 1 | 1 | 1 |
| Synthesis 9 | 1 | 1 | 1 | 1 | 1 | 1 | 1 | 1 |
| Synthesis 10 | 1 | 1 | 1 | 1 | 1 | 1 | 1 | 1 |
| Comparative Products | | | | | | | | |
| Synthesis 11 | 1 | 2 | 1 | 2 | 1 | 1B | 1 | 1 |
| Synthesis 12 | 1 | 1B | 1 | 1 | 1 | 1 | 1 | 1 |
| Synthesis 13 | 1 | 1B | 1 | 1 | 1 | 1 | 1 | 1 |
| Non-Addition | 1 | 1 | 1 | 1 | 1 | 1 | 1 | 1 |

As is clear from Table 4, the products of this invention demonstrate superior moisture separation in comparison to the comparative products.

EMBODIMENT 4

Actual Running Test 1

An evaluation of thermal decomposition and an actual running test were conducted according to the methods indicated below on each of the gasoline additives indicated in Table 5. Those results are indicated in Table 5.

(1) Evaluation of Thermal Decomposition

Thermal decomposition was evaluated by placing 1 g of the gasoline additive on an aluminum disk having a diameter of 5 cm, placing the disk on a heating plate maintained at a temperature of 280° C., removing the disk after 30 minutes, allowing the disk to cool, and then examining the appearance of the disk.

Evaluation of the appearance of the disk was made based on the standards indicated below.

When non-combustible residue remained: ×
A slight amount of combustion residue remained: ○
Hardly any combustion residue remained: ⊙

(2) Actual Running Test

1% by weight with respect to the gasoline of each of the additives were placed in the gasoline in a gasoline tank (61 liters) of a vehicle which was driven on ordinary roads. The states of the air intake system (intake valves, intake ports) and combustion chambers were evaluated before and after testing by disassembling the engine and visually confirming the degree of removal of deposits. An 1800cc Toyota Carina (Engine Type: 1S) was used for the test vehicle.

Evaluation of the degree of removal of deposits both before and after the testing was performed based on the standards indicated below.

×: Large increase in amount of deposits
—: No change
○: Some deposit removal effects
⊙: Large deposit removal effects
Δ: A little part of deposits removed

TABLE 5

| Gasoline Additive*[1] | Thermal Decomposition | Degree of Deposit Removal | | | | |
|---|---|---|---|---|---|---|
| | | Intake Valves | Intake Ports | Upper Comb. Chamber | Piston Heads | carburetter |
| Products of This Invention: | | | | | | |
| Blend of Synthesis 6 | ⊙ | ○ | ⊙ | ⊙ | ○ | ⊙ |
| Blend of Synthesis 8 | ○ | ⊙ | ⊙ | ○ | ⊙ | ⊙ |
| Blend of Synthesis 9 | ○ | ○ | ⊙ | ○ | ○ | ⊙ |
| Blend of Synthesis 10 | ⊙ | ○ | ⊙ | ○ | — | ⊙ |
| Comparative Products: | | | | | | |
| Blend of Synthesis 12 | × | × | ○-× | × | × | Δ |
| Blend of Synthesis 13 | × | × | ○ | × | × | Δ |
| Products of This Invention: | | | | | | |
| Synthesis 6, Unblended | ⊙ | ○ | ○ | ○ | — | ⊙ |
| Synthesis 8, Unblended | ○ | ○ | ○ | ○ | — | ⊙ |

TABLE 6

| additive | thermal decomposition | degree of deposit removal | | | | |
|---|---|---|---|---|---|---|
| | | intake valve | intake port | upper part of combustion chamber | piston head | carburetter |
| compound 14 | ○ | ○ | ⊙ | ○ | Δ | ⊙ |
| 15 | ○ | Δ | ○ | ○ | — | ⊙ |
| 16 | ○ | Δ | ○ | ○ | — | ⊙ |
| 17 | ○ | ○ | ○ | ○ | Δ | ○ |
| 18 | ○ | ○ | ○ | ○ | Δ | ○ |
| 19 | ○ | Δ | ○ | Δ | — | ○ |
| 20 | ○ | ○ | ○ | ○ | Δ | ⊙ |
| 21 | ○ | ○ | ○ | ○ | — | ⊙ |
| 22 | ○ | ○ | ○ | Δ | — | ⊙ |
| 26 | ○ | ○ | ○ | Δ | Δ | ⊙ |
| blend of 14 | ⊙ | ⊙ | ⊙ | ⊙ | ⊙ | ⊙ |

TABLE 6-continued

| additive | thermal decomposition | degree of deposit removal | | | | |
|---|---|---|---|---|---|---|
| | | intake valve | intake port | upper part of combustion chamber | piston head | carburetter |
| blend of 16 | ⊙ | ⊙~○ | ⊙ | ⊙ | ○ | ⊙ |
| blend of 18 | ⊙ | ⊙ | ⊙ | ⊙ | ○ | ⊙ |
| blend of 20 | ⊙ | ⊙~○ | ⊙ | ⊙~○ | ⊙~○ | ⊙ |
| nonylphenol (BO)15 50% | ⊙ | — | — | — | — | — |

*1 The additive marked by "unblended" was used in 50% dilution with an organic solvent. That marked by "blended" was used in the following formulation.

| | |
|---|---|
| Ethylamine obtained from Gerbe reaction in each of the syntheses | 1 part by weight |
| 15 mole butylene oxide addition product of nonylphenol [Nonylphenol (BO)$_{15}$] | 1 part by weight |
| Aromatic solvent | 2 parts by weight |

Results in Table 5 show that the invention exhibits a satisfactory removal of the deposits.

EMBODIMENT 4-2

Actual running test 2

The compounds 14 to 22 and 26 were examined in the same way as shown in Embodiment 4. Results are shown in Table 6. It is seen in the data of Tables 5 and 6 that the additive of the invention presented a good deposit-removing effect and the blends of the additive of the invention provided a more improved result. The blend is good at the thermal decomposition.

EMBODIMENT 5

Actual running test 3

Various gasoline additive components were manufactured by mixing the compound of Synthesis 6, the compound of Synthesis 8, nonylphenol(BO)15, and an aromatic solvent in the proportions indicated in Table 5.

Actual running tests were performed on these components according to the same testing method as that of Embodiment 4 and 4-2. Results are shown in Table 7.

EMBODIMENT 6

Actual running test 4

This is an application to Diesel light oil. Tests 1 to 15 were carried out with the compounds of the syntheses 1 to 10 and the compounds 14 to 18 in the form of its 50% dilution by an aromatic solvent. Tests 16 to 18 were conducted with a blend of the compound of the synthesis 8 an adduct of 15 moles of butylene oxide and nonylphenol and an aromatic solvent. Test 19 included no additive.

TEST METHOD

Each additive was tested in view of cleaning performance of coked matters at an injection nozzle of a Diesel engine. One percent by weight of each additive was added to a commercially available light oil. Cars, Corolla of Toyota (tradename) having an exhaust capacity of 1.83 liters, were run with the respective mixed oils for 500 km in an urban area. A flow amount of air through the injection nozzle at a needle lift amount of 0.2 mm was determined before the running and after the running. An air flow ratio to an air flow amount of the used nozzle to that of a fresh nozzle was determined to find a cleaning result of the coked matters. Results are shown in Table 8.

It is noted from the data of Table 8 that the additives of the invention can clean the injection nozzle of the coked matters and recovered an air flow amount. In addition, the additives of the invention provide an anti-corrosive effect to the Diesel light oil and the water-separating effect when water is involved.

TABLE 7

| composition | additive composition (wt. %) | | | | degree of removal of deposits | | | |
|---|---|---|---|---|---|---|---|---|
| | synthesis example 6 | synthesis example 8 | nonylphenol (BO)15 | aromatic solvent | intake valve | intake port | upper part of combustion | piston head |
| 1 | 15 | 0 | 25 | 60 | ○ | ○ | ○ | ○ |
| 2 | 25 | 0 | 25 | 50 | ○ | ⊙ | ⊙ | ○ |
| 3 | 10 | 5 | 25 | 60 | ○ | ⊙ | ⊙ | ○~⊙ |
| 4 | 0 | 10 | 25 | 65 | ○ | ○~⊙ | ○ | ○~⊙ |
| 5 | 5 | 10 | 25 | 60 | ○ | ○~⊙ | ○~⊙ | ○~⊙ |
| 6 | 0 | 15 | 25 | 60 | ○~⊙ | ⊙ | ○ | ⊙ |
| 7 | 5 | 15 | 25 | 55 | ○~⊙ | ⊙ | ○~⊙ | ⊙ |
| 8 | 10 | 15 | 25 | 50 | ○~⊙ | ⊙ | ⊙ | ⊙ |
| 9 | 5 | 20 | 25 | 50 | ⊙ | ⊙ | ⊙ | ⊙ |
| 10 | 0 | 25 | 25 | 50 | ⊙ | ⊙ | ○ | ⊙ |
| 11 | 5 | 20 | 5 | 70 | ⊙ | ⊙ | ⊙ | ⊙ |
| 12 | 5 | 20 | 12.5 | 62.5 | ⊙ | ⊙ | ⊙ | ⊙ |
| 13 | 5 | 20 | 30 | 45 | ⊙ | ⊙ | ⊙ | ○~⊙ |

It is seen in the data of Table 7 that the mixture of the compound of the synthesis 6 and the compound of the synthesis 8 provided an improved deposit-removing effect.

TABLE 8

| test No. | additive | air flow ratio | |
|---|---|---|---|
| | | before test | after test |
| 1 | 50% dilution of synthesis 1 | 21 | 73 |
| 2 | " 2 | 19 | 62 |
| 3 | " 3 | 20 | 63 |
| 4 | " 4 | 19 | 66 |
| 5 | " 5 | 21 | 74 |

TABLE 8-continued

| test No. | additive | | air flow ratio | |
|---|---|---|---|---|
| | | | before test | after test |
| 6 | " | 6 | 22 | 78 |
| 7 | " | 7 | 18 | 68 |
| 8 | " | 8 | 19 | 77 |
| 9 | " | 9 | 20 | 74 |
| 10 | " | 10 | 21 | 75 |
| 11 | 50% dilution of compound | 14 | 19 | 76 |
| 12 | " | 15 | 20 | 69 |
| 13 | " | 16 | 21 | 68 |
| 14 | " | 17 | 20 | 66 |
| 15 | " | 18 | 21 | 71 |
| 16* | blend of synthesis | 8 | 18 | 92 |
| 17* | " | 8 | 20 | 94 |
| 18* | " | 8 | 21 | 89 |
| 19 | no additive | | 22 | 20 |

The composition of the tests 16 to 18 are shown below.

| test No. | compound of synthesis 8 | nonylphenol (BO)15 | aromatic solvent |
|---|---|---|---|
| 16 | 10 wt % | 40 wt % | 50 wt % |
| 17 | 25 wt % | 25 wt % | 50 wt % |
| 18 | 40 wt % | 10 wt % | 50 wt % |

We claim:

1. A gasoline composition comprising gasoline and an additive for gasoline, which comprises a compound defined by formula (7), (8) or (9):

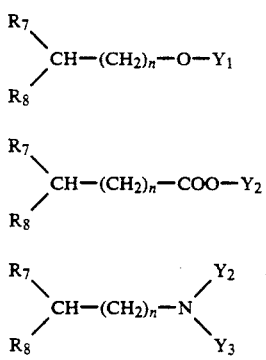

in which R7 and R8 are each a hydrocarbon group having 3 to 18 carbon atoms, provided that the sum total of the carbon number in R7 and R8 ranges from 8 to 36, n is zero or an integer of 1 to 4, Y1 is an amine group having formula (10) or an amineoxide group having formula (11), Y2 is hydrogen or has formula (12) or (13), with the proviso that Y2 cannot be hydrogen in formula (8), and Y3 has formula (12) or (13):

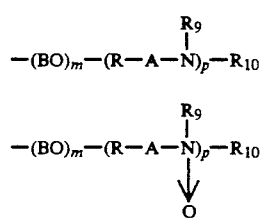

$$-(BO)_{m+1}-(R-A-N)_p-R_{10} \quad (12)$$
$$\overset{|}{R_9}$$

$$-(BO)_{m+1}-(R-A-N)_p-R_{10} \quad (13)$$
$$\overset{|}{R_9}$$
$$\downarrow$$
$$O$$

in which B is an alkylene having 3 to 4 carbon atoms, m is zero or an integer of 1 to 3, R does not exist or is —CH2CONH—, —CH2CH(OH)— or —CH2CO—, A does not exist or is an alkylene having 1 to 4 carbon atoms, R9 and R10 are each hydrogen, an alkyl having 1 to 4 carbon atoms or a hydroxyalkyl having 1 to 4 carbon atoms and p is 1 or 2.

2. The gasoline composition as claimed in claim 1, which further comprises a carrier oil defined by one of the following formulae:

$$R_9-O(DO)_d-R' \quad R_9-O(DO)_d-OCR',$$

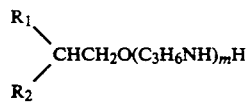

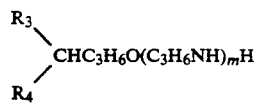

in which R9 and R10 are each having 1 to 30 carbon atoms, R' is hydrogen or an alkyl having 1 to 20 carbon atoms, D is an alkylene having 3 to 4 carbon atoms and d is an integer of 1 to 50.

3. The gasoline composition as claimed in claim 1, wherein the additive for gasoline comprises a mixture of the compound in which R7 and R8 are each a straight chain hydrocarbon and the compound in which R7 and R8 are each a hydrocarbon containing a branched methyl.

4. The gasoline composition as claimed in claim 1, in which the additive for gasoline comprises a compound defined by formula (1) or 2):

$$\underset{R_2}{\overset{R_1}{\diagdown}}CHCH_2O(C_3H_6NH)_mH \quad (1)$$

in which R1 and R2 each a hydrocarbon group having 3 to 16 carbon atoms, provided that the sum total of the carbon number in R1 and R2 ranges from 10 to 32, and m is 1 or 2, $$\underset{R_4}{\overset{R_3}{\diagdown}}CHC_3H_6O(C_3H_6NH)_mH \quad (2)$$

in which R3 and R4 are each a hydrocarbon group having 3 to 15 carbon atoms, provided that the sum total of the carbon number in R3 and R4 ranges from 8 to 30, and m is 1 or 2.

* * * * *